United States Patent [19]

Omura et al.

[11] Patent Number: 4,948,782

[45] Date of Patent: Aug. 14, 1990

[54] A METHOD OF PROMOTING THE GROWTH OF DOMESTIC ANIMALS WITH ERYTHROMYCIN DERIVATIVE CONTAINING COMPOSITION

[75] Inventors: Satoshi Omura, Tokyo; Zen Itoh, Maebashi, both of Japan

[73] Assignee: Kitasato Kenkyusho, Tokyo, Japan

[21] Appl. No.: 158,163

[22] Filed: Feb. 18, 1988

[30] Foreign Application Priority Data

Feb. 20, 1987 [JP] Japan .................................. 62-35469

[51] Int. Cl.[5] .............................................. A61K 31/70

[52] U.S. Cl. ....................................... 514/29; 536/7.2; 536/7.4

[58] Field of Search ..................... 536/7.2, 7.4; 514/29

[56] References Cited

U.S. PATENT DOCUMENTS 4,588,712 5/1986 Toscano .............................. 536/7.2

FOREIGN PATENT DOCUMENTS 0215355 3/1987 European Pat. Off. ............ 536/7.2

*Primary Examiner*—Ronald W. Griffin

*Assistant Examiner*—Elli Peselev

*Attorney, Agent, or Firm*—David G. Conlin; Ernest V. Linek

[57] ABSTRACT

A growth promoting composition for animals containing an erythromycin derivative wherein a dimethylamino radical of the 3'-position is converted into a primary amino radical, a secondary amino radical, a tertiary amino radical other than the dimethyl amino radical, or a quaternary ammonio radical.

This composition does not exhibit the antimicrobial activity at all or show the extremely decreased antimicrobial activity, and has the excellent effect to improve the feed efficiency of domestic animals.

4 Claims, No Drawings

A METHOD OF PROMOTING THE GROWTH OF DOMESTIC ANIMALS WITH ERYTHROMYCIN DERIVATIVE CONTAINING COMPOSITION

FIELD OF THE INVENTION

This invention relates to a growth promoting composition and production thereof.

DESCRIPTION OF THE PRIOR ART

In order to promote the growth and improve the feed efficiency of domestic animals such as broilers, pigs and cattle, various antibiotics such as aureomycin and monensin are now frequently used.

The growth promoting effect of the antibiotics is achieved based on the antimicrobial activity of these antibiotics against various bacteria such as enterobacteria, which are present in digestive organs such as stomach and intestine. The antiobiotics stabilize or decrease their activity and, as a result, protect the nutrients from metabolization by the bacteria before the nutrients are absorbed in the animal bodies.

For example, a portion of hydrocarbons contained in the food orally taken by the animal is metabolized by enterobacteria, and converted into acetic acid, propionic acid, butyric acid and the like through pyruvic acid. It is considered that a portion of the energy in the food is lost as methane, carbon dioxide or hydrogen, when acetic acid or butylic acid is produced. The antimicrobial activity of the antibiotics lowers the activity of the bacteria in the digestive organs to prevent the energy loss, and thereby the improvement of the feed efficiency is achieved.

The eggs and meat of these domestic animals contain the residual antibiotics having the antimicrobial activity. When the eggs and meat are used for food, the antibacterial substances which are essentially unnecessary are taken in the human body together with the food. There is the danger of causing the problems concerning public health such as the appearance of resistant bacterial strains against the antibiotics.

SUMMARY OF THE INVENTION

The present inventors found out that certain erythromycin derivatives had a strong motiline-like action and stimulated the contractile motion of the digestive tract, in spite of lacking or largely decreased antimicrobial activity. This time, the present inventors have further found that these erythromycin derivatives have the effects of promoting the growth of and improving the feed efficiency for domestic animals. The present inventors have found that these derivatives can be used as a means for solving the problems of the prior art described above.

That is to say, the present invention provides growth promoting composition for animals containing an erythromycin derivative wherein the dimethylamino radical at the 3'-position is converted into a primary amino radical, a secondary amino radical, a tertiary amino radical other than the dimethylamino radical or a quaternary ammonio radical.

As the above erythromycin derivative used in the present invention, there can be mentioned, for example, a compound represented by the general formula:

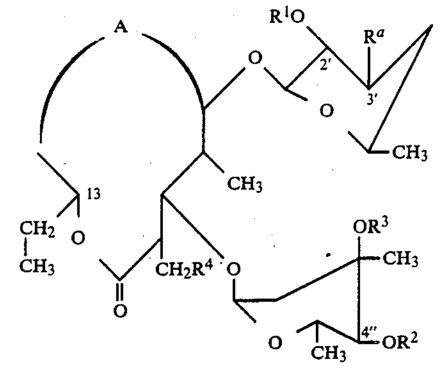

(I)

wherein $R^1$ stands for a hydrogen atom or an acyl radical which may be substituted; $R^2$ stands for a hydrogen atom, acyl or alkyl radical which may be substituted; $R^3$ stands for a hydrogen atom or a methyl radical; $R^4$ stands for a hydrogen atom or a hydroxy radical; $R^a$ stands for the formula

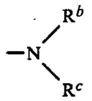

(wherein $R^b$ stands for a hydrogen atom, a lower alkyl or cycloalkyl radical, $R^c$ stands for a hydrogen atom, a lower alkyl, cycloalkyl, lower alkenyl or lower alkynyl radical which may be substituted, or $R^b$ and $R^c$ form a cyclic alkylamino radical together with the adjacent nitrogen atom, with the proviso that $R^c$ stands for a hydrogen atom, a lower alkyl, cycloalkyl, lower alkenyl or lower alkynyl radical which has two or more carbon atoms and may be substituted, when $R^b$ is a methyl radical) or the formula

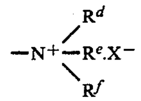

(wherein each of $R^d$, $R^e$ and $R^f$, which may be the same or different, stands for a lower alkyl, cycloalkyl, lower alkenyl or lower alkynyl radical which may be substituted, or $R^d$ and $R^e$ form a cyclic alkylamino radical together with the adjacent nitrogen atom, and $X^-$ stands for an anion);

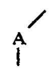

stands for the formula:

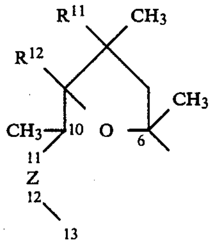

wherein Z stands for the formula

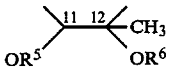

(wherein $R^5$ stands for a hydrogen atom, an acyl or alkyl radical which may be substituted, and $R^6$ stands for a hydrogen atom, an acyl radical of a lower carboxylic acid or an alkyl radical which may be substituted by an alkylthio radical), the formula

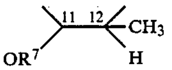

(wherein $R^7$ stands for a hydrogen atom, an acyl or alkyl radical which may be substituted),

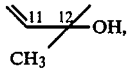 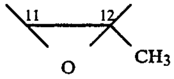 or 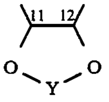

wherein Y stands for the formula

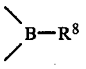

(wherein $R^8$ stands for an alkyl or aryl radical),

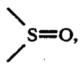, 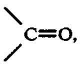, 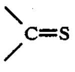

or the formula

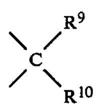

wherein each of $R^9$ and $R^{10}$, which may be the same or different, stands for a hydrogen atom or an alkyl radical, or forms a cyclic alkyl radical with the adjacent carbon atom, or either of $R^9$ and $R^{10}$ is a hydrogen atom, an alkyl or aryl radical while the other is a dialkylamino radical, both $R^{11}$ and $R^{12}$ stand for hydrogen atoms or both taken together form a chemical bond, or the formula:

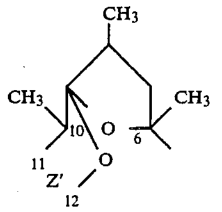

wherein Z′ stands for the formula

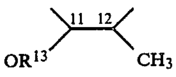

(wherein $R^{13}$ stands for a hydrogen atom, an acyl or alkyl radical which may be substituted). An erythromycin derivative having the basic skeleton represented by the formula (I) is also referred to as an anhydroerythromycin derivative.

The compound (I) is characterized by a primary, secondary or tertiary amino radical, or a quaternary ammonio radical at the 3′-position, each of which does not naturally occur, whereas natural erythromycin has a dimethylamino radical at the 3′-position.

The acyl radical represented by $R^1$ in the foregoing formula may be a carboxylic acyl, sulfonic acyl, phosphorous acyl or phosphoric acyl radical.

The acyl radical represented by $R^2$, $R^5$ or $R^7$ in the foregoing formula may be a carboxylic acyl or sulfonic acyl radical.

The carboxylic acyl is an acyl radical derived from a carboxylic acid, which may be a monocarboxylic or polycarboxylic acid, and a saturated or unsaturated carboxylic acid.

As the monocarboxylic acyl radical, there can be mentioned a saturated or unsaturated aliphatic acyl radical containing 1 to 20 carbon atoms (for example, formyl, acetyl, propionyl, butyryl, isobutyryl, valeryl, isovaleryl, hexanoyl, pivaloyl, lauroyl, myristoyl, palmitoyl, stearoyl, acryloyl, propioloyl, methacryloyl, etc.), an aryl carboxylic acyl radical (for example, benzene carboxylic acid, naphthalene carboxylic acid, etc.) and the like.

As the polycarboxylic acyl radical, there can be mentioned a saturated or unsaturated aliphatic dicarboxylic acyl radical having 2 to 6 carbon atoms, which may optionally be esterified, such as oxalo, carboxyacetyl, 3-carboxypropionyl, cis-3-carboxyacryloyl, trans-3-carboxyacryloyl, cis-3-methyl-3-carboxyacryloyl, etc.

The sulfonic acyl is an acyl radical derived from a sulfonic acid represented, for example, by the general formula $R^{14}SO_2$—, wherein $R^{14}$ stands for an alkyl, aryl or aralkyl radical. The alkyl radical preferably contains, for example, 1 to 6 carbon atoms, and may be linear or branched. Examples of the alkyl radicals are methyl, ethyl, propyl, isopropyl, butyl, isobutyl, sec-butyl, tert-butyl, n-pentyl and n-hexyl, Examples of the aryl radicals includes phenyl and naphthyl. The aryl radical may have a substituent and examples of the substituent include a lower alkyl radical such as methyl, a lower alkoxy radical such as methoxy, a halogen atom such as fluorine, chlorine and bromine, a nitro radical, a carboxy radical and the like. An example of the aralkyl is 2-phenethyl.

The phosphorous acyl is an acyl radical derived from phosphorous acid represented, for example, by the general formula $R^{15}OP(=O)H-$, wherein $R^{15}$ stands for a hydrogen atom, an alkyl, aryl or aralkyl radical. The alkyl radical preferably contains, for example, 1 to 6 carbon atoms and may be linear or branched. Examples of the alkyl radicals include methyl, ethyl, propyl, isopropyl, butyl, isobutyl, sec-butyl, tert-butyl, n-pentyl and n-hexyl. Examples of the aryl radicals include phenyl, tolyl and naphthyl. As the aralkyl radical, there can be mentioned an aryl alkyl radical, wherein the aryl is preferable to be the above-mentioned aryl and the alkyl is preferable to be an alkyl radical having 1 to 3 carbon atoms such as methyl, ethyl or propyl.

The phosphoric acyl is an acyl radical derived from phosphoric acid, which is represented, for example, by the general formula $(R^{16}O)_2 P(=O)-$, wherein $R^{16}$ has the same meaning as $R^{15}$.

As the substituent represented by $R^1$, $R^2$, $R^5$ and $R^7$ in the acyl radical, which may be substituted, there can be mentioned, for example, a halogen atom, an alkoxy or alkylthio radical. Examples of the halogen atoms include chlorine, bromine, fluorine and iodine. As the alkoxy radical, there can be mentioned radicals containing 1 to 4 carbon atoms, such as methoxy, ethoxy, propoxy and butoxy. As the alkylthio radical, there can be mentioned radicals containing 1 to 4 carbon atoms, such as methylthio, ethylthio, propylthio, isopropylthio, butylthio, isobutylthio, sec-butylthio and tert-butylthio.

As the lower carboxylic acyl radical represented by $R^6$ in the foregoing formula, there can be mentioned a monocarboxylic acyl or polycarboxylic acyl radical containing 1 to 6 carbon atoms, such as formyl, acetyl, propionyl, butyryl, isobutyryl, valeryl, isovaleryl, hexanoyl, oxalo, carboxyacetyl or 3-carboxypropionyl.

In the foregoing formula, the alkyl radical represented by $R^2$, $R^5$ or $R^7$, which may be substituted, is preferable to have 1 to 3 carbon atoms and may be linear or branched. Examples of the alkyl radicals include methyl, ethyl, propyl, and isopropyl. The substituent is preferably an alkoxy radical containing 1 to 3 carbon atoms or an alkoxyalkoxy radical containing 2 to 6 carbon atoms. Examples of the alkoxy radicals include methoxy, ethoxy and propoxy, while examples of the alkoxyalkoxy radicals include methoxyethoxy, methoxypropoxy, methoxybutoxy, methoxypentyloxy, ethoxyethoxy, ethoxypropoxy, ethoxybutoxy and propoxypropoxy.

In the foregoing formula, the alkyl radical represented by $R^6$, which may have an alkylthio substituent, can be methyl. The alkylthio as the substituent may include a radical represented by the general formula $R^{17}S-$, wherein $R^{17}$ is a lower alkyl radical. The lower alkyl radical is preferable to contain 1 to 3 carbon atoms, such as methyl, ethyl or propyl.

In the foregoing formula, the alkyl radical represented by $R^8$ may contain 1 to 6 carbon atoms, preferably 1 to 3 carbon atoms, and examples thereof include methyl, ethyl and propyl. The aryl radical represented by $R^8$ is, for example, phenyl, tolyl or naphthyl.

As the alkyl radical represented by $R^9$ and $R^{10}$ in the foregoing formula, there can be mentioned a radical which has 1 to 6 carbon atoms and may be linear or branched, and examples thereof include methyl, ethyl, propyl, isopropyl, butyl, isobutyl, sec-butyl, tert-butyl, n-pentyl and n-hexyl. Among these preferred is a linear or branched radical containing 1 to 3 carbon atoms, such as methyl, ethyl, propyl, or isopropyl.

In the foregoing formula, the carbon chain represented by $R^9$ and $R^{10}$ for forming a cyclic alkyl together with the carbon atom in the acetal bond may have 4 to 5 carbon atoms, including tetramethylene, pentametylene, etc.

In the foregoing formula, the aryl radical represented by $R^9$ and $R^{10}$ is, for example, phenyl, tolyl, or naphthyl.

As the dialkylamino radical represented by $R^9$ and $R^{10}$ in the foregoing formula, there can be mentioned a radical represented by the general formula $-NR_2^{18}$, wherein $R^{18}$ stands for a lower alkyl radical. The lower alkyl radical may contain 1 to 3 carbon atoms, such as methyl, ethyl or propyl.

As to $R^a$ in the foregoing formula, the lower alkyl radical represented by $R^b$ or $R^d$ is preferable to be a radical having 1 to 6 carbon atoms, and examples thereof include methyl, ethyl, propyl, isopropyl, butyl, isobutyl, sec-butyl, pentyl, isopentyl and hexyl.

The lower alkyl radical represented by $R^e$ or $R^f$, which may have a substituent, is preferable to be a radical having 1 to 6 carbon atoms, and examples thereof include methyl, ethyl, propyl, isopropyl, butyl, isobutyl, pentyl and hexyl.

In the foregoing formula, the substituted or unsubstituted cycloalkyl radical represented by $R^b$, $R^e$, or $R^f$ may contain 3 to 7 carbon atoms, and examples thereof include cyclopropyl, cyclobutyl, cyclopentyl, cyclohexyl and cycloheptyl, preferably those having 4 to 6 carbon atoms, namely cyclobutyl, cyclopentyl and cyclohexyl.

The lower alkenyl radical represented by $R^e$ or $R^f$, which may be substituted, is preferable to be a radical having 2 to 6 carbon atoms, and examples thereof include vinyl, allyl, 2-butenyl, methylallyl, 3-butenyl, 2-pentenyl, 4-pentenyl and 5-hexenyl.

The lower alkynyl radical represented by $R^e$ or $R^f$, which may be substituted, is preferable to be a radical having 2 to 6 carbon atoms, and examples thereof include ethynyl, propargyl, 2-butyn-1-yl, 3-butyn-1-yl, 3-butyn-2-yl, 1-pentyn-3-yl, 3-pentyn-1-yl, 4-pentyn-2-yl and 3-hexyn-1-yl.

The substituents in the foregoing alkyl, cycloalkyl, alkenyl and alkynyl radicals include, for example, hydroxy, $C_{3-6}$cycloalkyl, $C_{6-10}$aryl, $C_{1-4}$alkoxy, $C_{1-4}$alkoxy-$C_{2-3}$alkyl, $C_{3-6}$cycloalkyloxy, $C_{6-10}$aryloxy, $C_{7-12}$aralkyloxy, $C_{1-4}$alkylthio, $C_{3-6}$cycloalkylthio, $C_{6-10}$arylthio, $C_{7-12}$aralkylthio, amino, monoC$_{1-4}$alkylamino, diC$_{1-4}$alkylamino, $C_{3-6}$cycloalkylamino, $C_{6-10}$arylamino, $C_{7-12}$aralkylamino, azido, nitro, halogen, cyano, carboxy, $C_{1-4}$alkoxycabonyl, $C_{6-10}$aryloxycarbonyl, $C_{3-6}$cycloalkyloxycarbonyl, $C_{7-12}$aralkyloxycarbonyl (CO in these carbonyl groups may be acetalyzed), $C_{1-5}$alkanoyl, formyloxy, $C_{1-4}$alkylsulfinyl, $C_{6-10}$arylsulfinyl, $C_{1-4}$alkylsulfonyl, $C_{6-10}$arylsulfonyl, $C_{1-15}$alkanoyloxy, sulfo carbamoyl, carbamoyl which may be substituted, carbamoyloxy, carbamoyloxy which may be substituted, formylamino, $C_{1-4}$ alkanoylamino, $C_{6-10}$arylcarbonylamino, $C_{1-4}$alkoxycarbonylamino, $C_{7-12}$aralkyloxycarbonylamino, oxo, epoxy, thioxo, sulfonamido, heterocyclic radical, heterocyclic thio, heterocyclic carbonylamino, heterocyclic oxy, heterocyclic amino, $C_{1-4}$alkoxycarbonyloxy, $C_{1-4}$alkylsulfonyloxy, $C_{6-10}$arylsulfonyloxy, sulfoamino, sulfamoylamino, ureido and silyloxy.

The cycloalkyl, aryl, $C_{1-4}$alkyl and heterocyclic radicals which may substitute to the alkyl, alkenyl, alkynyl or cycloalkyl described above may further be substituted. Examples of such substituents are hydroxy, $C_{1-4}$alkyl (which may be substituted, and the substituent in this case is the same as the substituent in the alkyl as described above; the radical containing $C_{1-4}$alkyl as hereinafter mentioned may also have the same substituent), $C_{1-4}$alkoxy, $C_{1-4}$alkylthio, amino, $C_{1-4}$alkylamino, di$C_{1-4}$alkylamino, $C_{6-10}$arylamino, azido, nitro, halogen, oxo, cyano, carboxy, $C_{1-4}$alkoxycarbonyl, $C_{6-10}$aryloxycarbonyl, $C_{1-5}$alkanoyl, $C_{1-5}$alkanoyloxy, sulfo, carbamoyl, substituted carbamoyl, carbamoyloxy, $C_{1-4}$alkanoylamino, $C_{1-4}$alkoxycarbonylamino and sulfonylamino.

The number of the substituents on the foregoing respective radicals is preferably 1 to 3.

These substituents will be described in detail below.

Examples of the $C_{1-4}$alkyl radicals as the substituents include methyl, ethyl, propyl, isopropyl, butyl, isobutyl, sec-butyl and tert-butyl.

Examples of the $C_{3-6}$cycloalkyl radicals include cyclopropyl, cyclobutyl, cyclopentyl, and cyclohexyl.

Examples of the $C_{6-10}$aryl radicals include phenyl and naphtyl.

Examples of the $C_{1-4}$alkoxy radicals include methoxy, ethoxy, propoxy, isopropoxy, butoxy and tert-butoxy.

Examples of the $C_{3-6}$cycloalkyloxy radicals include cyclopropyloxy, cyclopentyloxy and cyclohexyloxy.

Examples of the $C_{6-10}$aryloxy radicals include phenoxy and nephtyloxy.

Examples of the $C_{7-12}$aralkyloxy radicals include benzyloxy, 2-phenethyloxy and 1-phenethyloxy.

Examples of the $C_{1-4}$alkylthio radicals include methylthio, ethylthio, propylthio and butylthio.

Examples of the $C_{3-6}$cycloalkylthio radicals include cyclopropylthio, cyclopentylthio and cyclohexylthio.

Examples of the $C_{6-10}$arylthio radicals include phenylthio and naphtylthio.

Examples of the $C_{7-12}$aralkylthio radicals include benzylthio, 2-phenethylthio and 1-phenethylthio.

Examples of the mono$C_{1-4}$alkylamino radicals include methylamino, ethylamino, propylamino, isopropylamino, butylamino, isobutylamino and tert-butylamino.

Examples of the di$C_{1-4}$alkylamino radicals include dimethylamino, diethylamino, dipropylamino, dibutylamino, N-methyl-N-ethylamino, N-methyl-N-propylamino and N-methyl-N-butylamino.

Examples of the $C_{3-6}$cycloalkylamino radicals include cyclopropylamino, cyclobutylamino, cyclopentylamino and cyclohexylamino.

Examples of the $C_{6-10}$arylamino radicals include anilino and the like.

Examples of the $C_{7-12}$aralkylamino radicals include benzylamino, 2-phenethylamino and 1-phenethylamino.

Examples of the halogen atoms include fluorine, chlorine, bromine and iodine.

Examples of the $C_{1-4}$alkoxycarbonyl radicals include methoxycarbonyl, ethoxycarbonyl, propoxycarbonyl, isopropoxycarbonyl, butoxycarbonyl, tert-butoxycarbonyl and isobutoxycarbonyl.

Examples of the $C_{6-10}$aryloxycarbonyl radicals include phenoxycarbonyl and the like.

Examples of the $C_{3-6}$cycloalkyloxycarbonyl radicals include cyclopropyloxycarbonyl, cyclobutyloxycarbonyl, cyclopentyloxycarbonyl and cyclohexyloxycarbonyl.

Examples of the $C_{7-12}$aralkyloxycarbonyl radicals include benzyloxycarbonyl, 1-phenethyloxycarbonyl and 2-phenethyloxycarbonyl.

Examples of the $C_{1-5}$alkanoyl radicals include formyl, acetyl, propionyl, butyryl and pivaloyl.

Examples of the $C_{1-15}$alkanoyloxy radicals include formyloxy, acetoxy, butyryloxy, pivaloyloxy, pentanoyloxy, hexanoyloxy, heptanoyloxy, octanoyloxy, nonanoyloxy, decanoyloxy, undecanoyloxy, dodecanoyloxy, tridecanoyloxy, tetradecanoyloxy and pentadecanoyloxy.

Examples of the substituted carbamoyl radicals include N-methylcarbamoyl, N,N-dimethylcarbamoyl, N-ethylcarbamoyl, N,N-diethylcarbamoyl, N-phenylcarbamoyl, pyrrolidinocarbonyl, piperidinocarbonyl, piperazinocarbonyl, morpholinocarbonyl and N-benzylcarbamoyl.

Examples of the substituted carbamoyloxy radicals include N-Methylcarbamoyloxy, N,N-dimethylcarbamoyloxy, N-ethylcarbamoyloxy, N-benzylcarbamoyloxy, N,N-dibenzylcarbamoyloxy and N-phenylcarbamoyloxy.

Examples of the $C_{1-4}$alkanoylamino radicals include formylamino, acetylamino, propionylamino and butyrylamino.

Examples of the $C_{6-10}$arylcarbonylamino radicals include benzoylamino and the like.

Examples of the $C_{1-4}$alkoxycarbonylamino radicals include methoxycarbonylamino, ethoxycarbonylamino, butoxycarbonylamino, and tert-butoxycarbonylamino.

Examples of the $C_{7-12}$aralkyloxycarbonylamino radicals include benzyloxycarbonylamino, 4-methoxybenzyloxycarbonylamino, 4-nitrobenzyloxycarbonylamino and 4-chlorobenzyloxycarbonylamino Examples of the sulfonylamino radicals include methanesulfonylamino, ethanesulfonylamino, butanesulfonylamino, benzenesulfonylamino, toluenesulfonylamino, naphthalenesulfonylamino, trifluoromethanesulfonylamino, 2-chloroethanesulfonylamino and 2,2,2-trifluoromethanesulfonylamino.

The heterocyclic radicals include a cyclic radical containing 1 to 5 nitrogen, oxygen or sulfur atoms, and examples thereof are pyrrolidinyl, pyrrolyl, pyrazolyl, imidazolyl, furyl, thienyl, oxazolyl, isooxazolyl, isothiazolyl, thiazolyl, piperidinyl, pyridyl, pyridazinyl, pyrazinyl, piperadinyl, pyrimidinyl, pyranyl, tetrahydropyranyl, tetrahydrofuryl, indolyl, quinolyl, 1,3,4-oxadiazolyl, thieno[2,3-d]pyridyl, 1,2,3-thiadiazolyl, 1,3,4-thiadiazolyl, 1,2,3-triazolyl, 1,2,4-triazolyl, 1,3,4-triazolyl, tetrazolyl, 1,3-dioxoranyl, tetrazolo[1,5-b]pyridazinyl, benzothiazolyl, benzooxazolyl, benzoimidazolyl, benzothienyl and morpholinyl.

As the heterocyclic thio, heterocyclic oxy, heterocyclic amino and heterocyclic carbonylamino radicals, there can be mentioned radicals having the above heterocyclic radicals bonded to sulfur atom, oxygen atom, nitrogen atom or carbonylamino radical, respectively.

Examples of the $C_{1-4}$alkylsulfonyloxy radicals include methanesulfonyloxy, ethanesulfonyloxy and butanesulfonyloxy.

Examples of the $C_{6-10}$arylsulfonyloxy radicals include benzenesulfonyloxy and toluenesulfonyloxy.

Examples of the silyloxy radicals include trimethylsilyloxy, t-butyldimethylsilyloxy and t-butyldiphenylsilyloxy.

Examples of the $C_{1-4}$alkylsulfinyl radicals include methylsulfinyl, ethylsulfinyl, propylsulfinyl and butylsulfinyl Examples of the $C_{6-10}$arylsulfinyl radicals include phenylsulfinyl and naphtylsulfinyl.

Examples of the $C_{1-4}$alkylsulfonyl radicals include methanesulfonyl, ethanesulfonyl and butanesulfonyl.

Examples of the $C_{6-10}$arylsulfonyl radicals include benzenesulfonyl and toluenesulfonyl.

Examples of the $C_{1-4}$alkoxycarbonyloxy radicals include methoxycarbonyloxy, ethoxycarbonyloxy and tert-butoxycarbonyloxy.

Further specific examples of the foregoing respective radicals include chloromethyl, bromomethyl, iodomethyl, trifluoromethyl, chloroethyl, bromoethyl, iodoethyl, chloropropyl, hydroxymethyl, hydroxyethyl, hydroxypropyl, 2-hydroxy-2-phenylethyl, cyclopropylmethyl, cyclobutylmethyl, cyclopentylmetyl, cyclohexylmethyl, 2-cyclohexylethyl, 3-chlorocyclobutylmethyl, benzyl, 4-chlorobenzyl, 4-nitrobenzyl, 4-methoxybenzyl, 2,4-dimethoxybenzyl, 3,4-dimethoxybenzyl, 4-methylbenzyl, 2-ethoxyethyl, 2-(2,2,2-trifluoroethoxy)ethyl, methoxymethyl, 2,2-dimethoxyethyl, 2,2-diethoxyethyl, cyclopropylmethoxymethyl, cyclobutylmethoxymethyl, 2-cyclopropylmethoxyethyl, 2-cyclobutylmethoxyethyl, 2-benzyloxyethyl, 3-benzyloxypropyl, 2-phenoxyethyl, 2-(2-phenethoxy)ethyl, 3-phenylpropyl, methylthiomethyl, 2-methylthioethyl, 2-phenylthioethyl, 2-benzylthioethyl, 2-butylthioethyl, cyclohexylthiomethyl, 2-(4-pyridylthio)ethyl, aminomethyl, 2-aminoethyl, 2-methylaminoethyl, 2-tert-butylaminoethyl, 2-dimethylaminoethyl, 3-dimethylaminopropyl, 2-cyclohexylaminoethyl, 2-benzylaminoethyl, 2-azidoethyl, nitromethyl, 2-nitroethyl, cyanomethyl, 2-cyanoethyl, 4-cyanobutyl, carboxymethyl, 2-carboxyethyl, ethoxycarbonylmethyl, phenoxycarbonylmethyl, cyclopentyloxycarbonylmethyl, acetylmethyl, benzoylmethyl, 4-chlorobenzoylmethyl, 3-(4-bromobenzoyl)propyl, 3-methoxybenzoylmethyl, 2-formyloxyethyl, 2-methylsulfinylethyl, 2-phenylsulfinylethyl, 2-methylsulfonylethyl, 3-phenylsulfonylpropyl, 2-acetoxyethyl, 4-acetoxybutyl, pivaloyloxymethyl, 3-sulfopropyl, carbamoylmethyl, 3-carbamoylpropyl, pyrrolidinocarbonylmethyl, 2-(N-ethyl-benzylamino)ethyl, 2-(2-oxopyrrolidino)ethyl, 2-formylaminoethyl, 3-formylaminopropyl, 3-trifluoroacetamidopropyl, 2-benzamidoethyl, 3-tert-butoxycarbonylaminopropyl, benzyloxycarbonylaminopropyl, 2,3-epoxypropy1,2-thioacetamidoethyl, 3-sulfoaminopropyl, 2-(1,3-dioxoran-2-yl)ethyl, 2-, 3-, 4-pyridylmethyl, 2-(4-pyridyl)ethyl, 3-(4-pyridyl)propyl, furfulyl, 3-(2-furyl)allyl, 3-(2-furyl)propyl, 2-(2-pyranyloxy)ethyl, 2-(3-indolyl)ethyl, 3-(1-indolyl)propyl, 3-(2-benzimidazolyl)propyl, 2-morpholinoethyl, (3-isoxazolyl)methyl, 2-(2-pyridylthio)ethyl, 2-(2-benzthiazolyl)ethyl, 2-(2-pyrimidinylthio)ethyl, 2-(2-amino-ethylthio)ethyl, 2-isonicotinoylaminoethyl, 2-thenoylaminoethyl, 2-furoylaminoethyl, 2-(tert-butoxycarbonyloxy)ethyl, 3-(tert-butoxycarbonyloxy)propyl, 2-methylsulfonyloxyethyl, 2-(p-toluenesulfonyloxy)ethyl, 2-(tert-butydimethylsilyloxy) ethyl, sulfoaminomethyl, 2-sulfoaminoethyl, ureidomethyl, 2-ureidoethyl, sulfamoylaminomethyl, 2-sulfamoylaminoethyl and (2-methoxyethoxy)methyl.

As to $R^a$ described above, examples of more preferable substituents in the lower alkyl, cycloalkyl, lower alkenyl and lower alkynyl radicals which may be substituted include halogen atoms (such as chlorine, bromine, iodine and fluorine), lower alkoxy radicals having 1 to 4 carbon atoms (such as methoxy, ethoxy, propoxy, isopropoxy and butoxy), lower alkylthio radicals having 1 to 4 carbon atoms (such as methylthio, ethylthio, propylthio and butylthio), aryl radicals (such as phenyl, tolyl and naphthyl), hydroxyl, alkoxycarbonyloxy radicals (such as tert-butoxycarbonyloxy), aralkyloxycarbonyloxy radicals (such as benzyloxycarbonyloxy), amino, substituted amino radicals (such as dimenthylamino and diethylamino), heterocyclic (cyclic amino) radicals (such as morpholino, piperidino, pyrrolidino and 2-oxopyrrolidino), acyloxy radicals having 1 to 3 carbon atoms (such as formyloxy, acetoxy and trifluoroacetoxy), acylamino radicals having 1 to 3 carbon atoms (such as acetamido and trifluoroacetamido), carboxy, lower ($C_{1-4}$) alkoxycarbonyl radicals (such as methoxycarbonyl, ethoxycarbonyl and butoxycarbonyl), carbamoyl, substituted carbamoyl radicals (such as N,N-dimethylcarbamoyl and N,N-diethylcarbamoyl), sulfo and the like.

In the foregoing formula, as the carbon chains represented by $R^b$ and $R^c$, or $R^d$ and $R^e$ for forming a cyclic alkylamino radical with the nitrogen atom at the 3'-position, there can be mentioned those having 3 to 6 carbon atoms such as trimethylene, tetramethylene, pentamethylene and hexamethylene.

In the foregoing formula, examples of the anions represented by $X^-$ include halogen ions (such as iodide ion, bromo ion and chloro ion), sulfate ion, phosphate ion, nitrate ion, methanesulfate ion, p-tolylsulfate ion, benzenesulfate ion, hydroxyl ion and organic carboxylate ions (such as oxalate ion, maleate ion, trifluoroacetate ion, lactobionate ion, acetate ion, propionate ion and ethylsuccinate ion).

In the compound (I) of the present invention, it is preferable that $R^1$ is a hydrogen atom or an alkyl carboxylic acyl radical having 1 to 5 carbon atoms; $R^2$ is a hydrogen atom, an alkyl carboxylic acyl radical having 1 to 5 carbon atoms, an alkyl sulfonic acyl radical having 1 to 5 carbon atoms or an alkylthiomethyl radical having 1 to 5 carbon atoms; $R^3$ is a methyl radical; $R^4$ is a hydrogen atom; Z is the formula

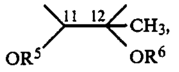

wherein each of $R^5$ and $R^6$ is a hydrogen atom, an alkyl carboxylic acyl radical having 1 to 5 carbon atoms or an alkyl sulfonic acyl radical having 1 to 5 carbon atoms, or $R^5$ and $R^6$ for

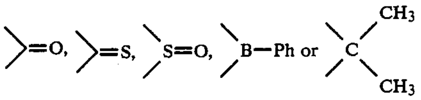

as Y; each of $R^d$ and $R^e$ is an alkyl radical having 1 to 3 carbon atoms, or $R^d$ and $R^e$ form a cyclic alkyl radical; $R^f$ is an unsubstituted or substituted alkyl radical having 1 to 5 carbon atoms, an alkenyl or alkynyl radical having 2 to 6 carbon atoms.

When $R^b$ and $R^c$ are different from each other, each of which is hydrogen or an alkyl radical having 1 to 3 carbon atoms, and form a secondary or tertiary amino radical as $R^a$, it is further preferable that both $R^1$ and $R^2$ are hydrogen, or $R^1$ is hydrogen or an alkyl carboxylic acyl radical and $R^2$ is hydrogen, and both $R^5$ and $R^6$ are hydrogen, or at least one of $R^5$ and $R^6$ is an alkyl carboxylic acyl radical having 1 to 5 carbon atoms. When $R^a$ is a quaternary ammonium salt, it is preferable that both $R^5$ and $R^6$ are hydrogen, or at least one of $R^5$ and $R^6$ is an alkyl carboxylic acyl radical having 1 to 5 carbon atoms.

In the compound (I) of the present invention, $R^a$ is preferable to be a quaternary ammonium salt. Particularly, it is preferable that $R^d$ and $R^e$ form a cyclic alkylamino radical of 5 to 7 members such as pyrrolidino, piperidino and hexamethyleneimino, or both $R^d$ and $R^e$ are alkyl radicals having 1 to 5 carbon atoms and $R^f$ is an alkyl radical having 1 to 5 carbon atoms, an alkenyl or alkynyl radical having 2 to 6 carbon atoms. When they have a substituent, it is particularly preferable to be hydroxy, carboxy, $C_{1-4}$alkoxycarbonyl, halogen, cyano and so on. As X of the quaternary ammonium salt, there are preferably mentioned chlorine, bromine and iodine.

Although processes for preparing the above compounds (I) and physicochemical properties thereof are described in European Patent Publication No. EP-A-No. 0 213 617 in detail, the compounds can be prepared by the processes which will hereinafter briefly described or the suitable combination thereof.

The compound wherein $R^a$ is $-NHCH_3$ or $-NH_2$ can be obtained by allowing a compound wherein the corresponding $R^a$ is $-N(CH_3)_2$ to react with iodine under basic conditions.

The compound wherein $R^a$ is a tertiary amino radical of

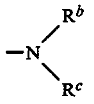

and the compound wherein $R^b$ in $-NHR^b$ is a secondary amino radical other than methyl can be prepared by subjecting a compound wherein $R^a$ is $-NHCH_3$ or $-NH_2$ to N-alkylation, N-alkenylation or N-alkynylation. These reactions may be carried out by allowing a corresponding ketone or aldehyde to react with a compound wherein $R^a$ is $-NHCH_3$ or $-NH_2$ under reducing conditions (for example, under the catalytic reducing conditions wherein palladium carbon is used as the catalyst) according to, for example, the methods described in R. K. Clark Jr. and M. Flyfelder, Antibiotics and Chemotherapy, 7, 483 (1957). Also the reactions can be conducted by allowing, for example, a corresponding alkyl, alkenyl or alkynyl halide to react with a compound wherein $R^a$ is $-NHCH_3$ or $-NH_2$, in the presence of a base (such as diisopropyl ethylamine). The alkylation, alkenylation or alkynylation in the latter processes is carried out by using about 1 to 100 mol equivalent, preferably about 2 to 25 mol equivalent of the reaction reagent per 1 mol of the starting compound, in a halogenated hydrocarbon solvent such as dichloromethane, at a temperature of about 0° to 100° C., preferably at room temperature (about 15° to 25° C.) to about 80° C. The reaction time is about 2 to 48 hours.

By subjecting a tertiary amine compound wherein $R^a$ is

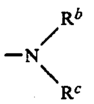

to these reactions, a compound wherein $R^a$ is

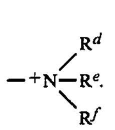

$NX^-$ can be prepared. Examples of the reagents to be used in the reactions include a corresponding alkyl, alkenyl or alkynyl halide, and iodine is preferable as a halogen. However, in case of a reactive alkenyl or alkynyl halide, chlorine or bromine is also preferably used (for example, allyl bromide and propargyl chloride). The solvent and reaction temperature are employed according to those described above. However, the reaction time is about 2 hours to about 1 week.

Of the present compounds, a compound wherein

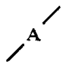

is

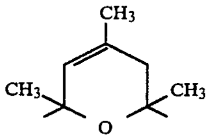

or

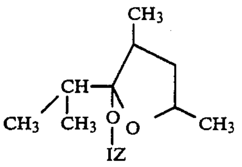

can be prepared by treating a compound wherein the corresponding

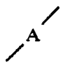

is

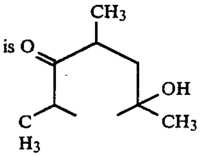

with an acid such as acetic acid [references: P. Kurath et al., Experientia, 27, 362 (1972); and K. Krowichki and A. Zamojiski, The Journal of Antibiotics, 26, 569 (1973)].

Further, a compound wherein

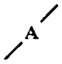

is

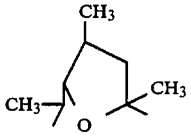

can be obtained by subjecting a compound wherein

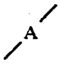

is

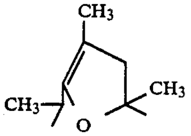

to the catalytic reduction wherein a platinum catalyst is used (see Japanese Unexamined Patent Publication No. 1588/1974).

Of the compounds used in the present invention, a compound wherein $R^1$, $R^2$, $R^5$ and $R^6$ are acyl (including sulfonyl) or alkyl, and a compound wherein $R^5$ and $R^6$ form a boronate, a carbonate, a sulfinate or a ketal can be prepared by subjecting a starting compound wherein the respectively corresponding $R^1$, $R^2$, $R^5$ and $R^6$ which may be protected are hydrogen to a known reaction, namely by allowing to react with an acylating agent (for example, a carboxylic acid anhydride such as acetic anhydride), an alkylating agent (for example, an alkyl iodide such as methane iodide, and dimethyl sulfoxide and acetic anhydride), a boronating agent (for example, phenylboric acid), a carbonating agent (for example, ethylene carbonate), a sulfinylating agent (for example, ethylene sulfite) or a ketalyzing agent (for example, 2-methoxypropene), followed by the removal of protection, if necessary.

The acylating reaction is preferably conducted in a solvent in the presence of a base. As the preferable solvent, there can be mentioned, for example, dichloromethane and pyridine, and as the preferable base, there can be mentioned, for example, pyridine and diisopropylethylamine. The reaction temperature is about 0° to 80° C., when allowed to react with an acylating agent derived from a carboxylic acid, and about 0° to 50° C., when allowed to react with an acylating agent derived from a sulfonic acid. The reaction time is about 10 minutes to about, 2 weeks, and about 10 minutes to about 2 days, respectively.

The reaction with the alkylating agent is also preferable to be conducted in a solvent. As the solvent, chloroform, dimethyl sulfoxide or the like is preferably employed. The reaction temperature is about 0° to 80° C., and the reaction time is about 15 minutes to about 1 week. A base is added therein as so desired, for accelerating the reaction and stabilizing the starting compound and/or the product. Examples of the preferable bases include pyridine and diisopropylethylamine.

In the boronation reaction, the boronating agent is preferably used in an amount of about 1 to 3 times that of the starting compound in molar ratio. This reaction is preferable to be conducted in a solvent such as benzene or toluene, at a reaction temperature of about 80° to 130° C., for a reaction time of about 1 to 5 hours.

In the carbonation reaction, the carbonating agent is preferably employed in an amount of about 2 to 10 times that of the starting compound in molar ratio. This reaction is preferably conducted in a solvent such as benzene or toluene, at a reaction temperature of about 25° to 130° C., for a reaction time of about 30 minutes to about 1 day. In case of employing ethylene carbonate as the carbonating agent, the addition of a base such as potassium carbonate is preferred.

In the sulfinylation reaction, the sulfinylating agent is preferably used in an amount of about 2 to 3 times that of the starting compound in molar ratio. For example, this reaction is preferably conducted in a solvent such as methanol or ethanol, at a reaction temperature of about 20° to 30° C., for a reaction time of about 2 to 3 days. Also in this reaction, the addition of a base such as potassium carbonate achieves good results often.

In the ketalization reaction, for example, chloroform is preferably employed as a solvent. The ketalyzing agent itself may be used as a solvent. The ketalyzing agent is used in an amount of about 2 to 100 times, preferably about 2 to 4 times, in molar ratio. This reaction is accelerated by adding, for example, pyridineum chloride as a catalyst. The reaction is preferably conducted at a temperature of about 0° to 80° C., more preferably about 15° to 25° C., for several hours to about 72 hours, more preferably about 12 to 24 hours.

In each of the reactions described above, the order of reactivity of hydroxyl radicals at the 2'-, 4"-, 11-, and 12-positions in the starting compounds, which may be protected, is $2' >> 4'' \geqq 11 >> 12$. By selecting the amount of the acylating agent or the alkylating agent, the reaction temperature and the reaction time, 1 to 4 hydroxyl radicals can be acylated or alkylated. Further, O-acetyl for the 2'-position, O-formyl for the 4"-position and O-silyl for the 4"- and 11-positions are used as protecting radicals which is removable by treating in methanol at room temperature to about 80° C. The compounds of the present invention can be prepared by using these processes singly or in combination.

The growth promoting composition for animals containing the erythromycin derivative of the present invention has the excellent effects of promoting the growth of and improving the feed efficiency for domestic animals such as cattle, pigs, sheep and chickens.

Further, the growth promoting composition of the present invention can be safely administered to the animals, because of its low toxicity and lacking or large decrease of antimicrobial activity.

Usually, for example, one or more kinds of the compounds (I) described above are mixed with a solid carrier or a liquid carrier so as to result in a final concentration of 0.00001 to 0.1% (w/w), particularly 0.0001 to 0.05% (1 to 500 ppm), and then fed to the animals.

As the solid carrier, there can be mentioned, for example, roughages such as hay, pasturage and silage, concentrated feeds such as grains (corn, barley, wheat, rye, oat and the like), oil cake (soybean cake, safflower cake and the like) and brans (rice bran, wheat bran and the like), milk sugar, cane sugar, grape sugar, yeasts, fish meal, talc, acid clay and clay. As the liquid carrier, there can be mentioned, for example, water, physiological salines and physiologically harmless organic solvents.

In addition, there may be added therein appropriate additives such as emulsifying agents, dispersing agents, suspending agents, wetting agents, thickening agents, gelling agents and solubilizing agents in a suitable amount. Further, antiseptics, bactericides, growth promoting composition such as vitamins, amino acids and synthetic estrogenic hormones, antibiotics for the treatment of diseases, enzyme preparations and lactic acid bacteria preparations may be incorporated therein.

When the compound (I) described above is mixed with other agents, the compound (I) may be mixed as it is. Also, the compound (I) can be mixed after previously diluted with the adjuvant such as milk sugar or as a premix containing the compound (I) (usually about 10% by weight).

When the erythromycin derivative of the present invention which is added in the feed is administered to the animals, its dose is normally about 0.0001 to 1 g/kg, preferably about 0.001 to 0.5 g/kg, though the suitable dose is selected according to the kind of animal, days of age, the kind of feed and so on.

The erythromycin derivatives used in the present invention are the derivatives of erythromycin which have largely decreased antimicrobial activity, while maintaining the improving effect of the feed efficiency of the animals, prepared by converting the dimethylamino radical of the 3'-position of the natural erythromycin into the primary amino radical, the secondary amino radical, the tertiary amino radical other than the dimethylamino radical or the quaternary ammonio radical. Therefore, the above derivatives can be said to be excellent as the growth promoting agent for the animals.

The growth promoting compositions for animals containing the erythromycin derivative of the present invention do not exhibit the antimicrobial activity at all or show an extremely decreased antimicrobial activity, and have the excellent effect to improve the feed efficiency for the domestic animals and the like.

Description of the Preferred Embodiments

Experimental Example 1

(Decreased Antimicrobial Activity of the Erythromycin Derivative)

The minimum inhibitory concentrations (MIC: mcg/ml) of the erythromycin derivatives of the present invention and the control erythromycin derivative (*) as the known growth promoting agent on typical test bacteria are shown in the following Tables 1 to 5. This result shows that the antimicrobial activity of the erythromycin derivatives used in the present invention are extremely weakened, compared with the control.

The test bacteria are abbreviated as follows:

SA(1): *Staphylococcus aureus* ATCC 6538P

SA(2): *Staphylococcus aureus* FDA 209P

BS: *Bacillus subtilis*

BC: *Bacillus cereus* IFO 3001

EC: *Escherichia coli* NIHJ

KP: *Klebsiella pneumoniae* ATCC 10031

TABLE 1-1

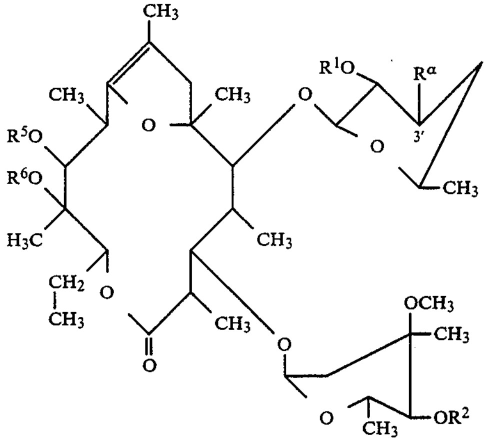

| | Compound (I) | | | | | MIC | | | | | |
|---|---|---|---|---|---|---|---|---|---|---|---|
| No. | $R^1$ | $R^2$ | $R^5$ | $R^6$ | $R^{\alpha}$ | SA (1) | SA (2) | BS | BC | EC | KP |
| 1 | H | H | H | H | 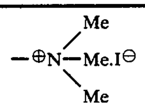 | >100 | >100 | >100 | >100 | >100 | >100 |
| 2 | H | H | $COCH_3$ | $COCH_3$ | 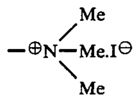 | 100 | 100 | 100 | 100 | >100 | >100 |
| 3 | H | H | $SO_2CH_3$ | H | 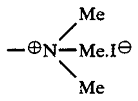 | >100 | >100 | >100 | >100 | >100 | >100 |
| 4 | H | CHO | $SO_2CH_3$ | H | 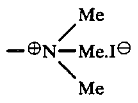 | >100 | >100 | >100 | >100 | >100 | >100 |
| 5 | H | H | H | H | 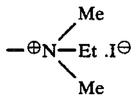 | >100 | >100 | >100 | >100 | >100 | >100 |
| 6 | H | H | H | H | 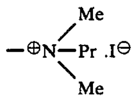 | >100 | >100 | >100 | >100 | >100 | >100 |
| 7 | $COCH_3$ | H | H | H | 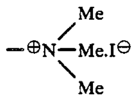 | 100 | >100 | >100 | >100 | >100 | >100 |

TABLE 1-1-continued
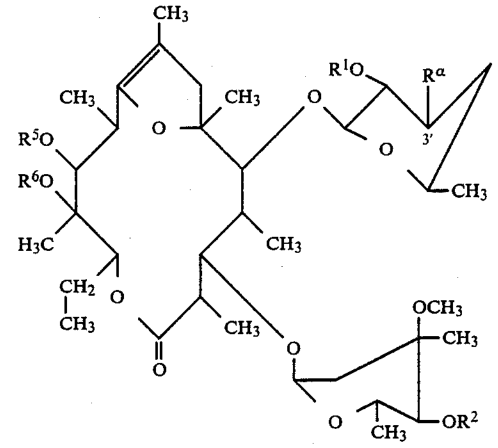
| | Compound (I) | | | | | MIC | | | | | |
|---|---|---|---|---|---|---|---|---|---|---|---|
| No. | $R^1$ | $R^2$ | $R^5$ | $R^6$ | $R^\alpha$ | SA (1) | SA (2) | BS | BC | EC | KP |
| 8 | H | H | H | H | $-NHCH_3$ | >100 | >100 | >100 | >100 | >100 | >100 |
| 9 | H | H | H | H | $-NH_2$ | >100 | >100 | >100 | >100 | >100 | >100 |
| 10 | H | H | H | H | 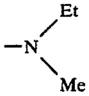 | >100 | >100 | >100 | >100 | >100 | >100 |
| 11 | H | H | H | H | 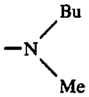 | >100 | >100 | >100 | >100 | >100 | >100 |
| 12 | H | H | H | H | 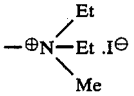 | >100 | >100 | >100 | >100 | >100 | >100 |
| 13 | H | H | H | H | 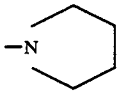 | >100 | >100 | >100 | >100 | >100 | >100 |
| 14 | H | H | H | H | 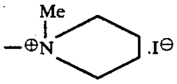 | >100 | >100 | >100 | >100 | >100 | >100 |
| 15 | H | H | H | H | 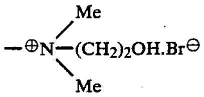 | >100 | >100 | >100 | >100 | >100 | >100 |
| 16 | H | H | H | H | 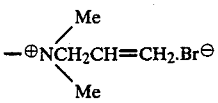 | 100 | >100 | >100 | >100 | >100 | >100 |
| 17 | H | H | H | H | 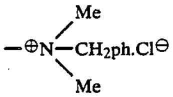 | 100 | 100 | 50 | 100 | >100 | >100 |
| 18 | H | H | $SO_2CH_3$ | H | 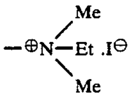 | >100 | >100 | >100 | >100 | >100 | >100 |

TABLE 1-1-continued
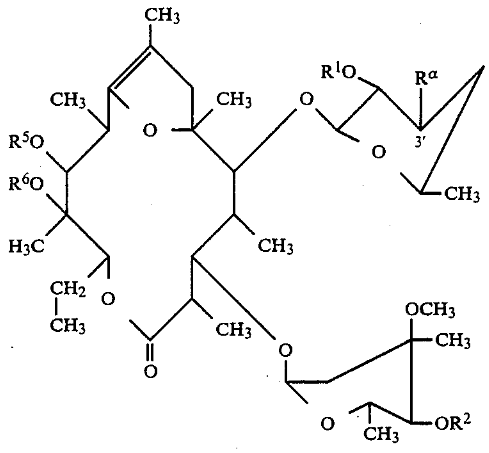
| | Compound (I) | | | | | MIC | | | | | |
|---|---|---|---|---|---|---|---|---|---|---|---|
| No. | $R^1$ | $R^2$ | $R^5$ | $R^6$ | $R^\alpha$ | SA (1) | SA (2) | BS | BC | EC | KP |
| 19 | H | H | H | H | 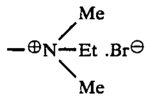 | >100 | >100 | >100 | >100 | >100 | >100 |
| 20 | H | H | H | H | $-NEt_2$ | >100 | >100 | >100 | >100 | >100 | >100 |
| 21 | H | H | H | H | —NHEt | >100 | >100 | >100 | >100 | >100 | >100 |
| 22 | H | H | H | H | 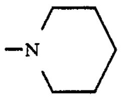 | >100 | >100 | >100 | >100 | >100 | >100 |
| 23 | H | H | H | H | 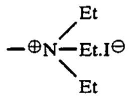 | >100 | >100 | >100 | >100 | >100 | >100 |
| 24 | H | H | H | H | 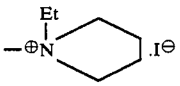 | >100 | >100 | >100 | >100 | >100 | >100 |
| 25 | H | H | H | H | 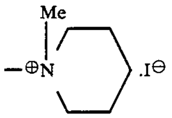 | >100 | >100 | >100 | >100 | >100 | >100 |
| 26 | H | H | H | H | 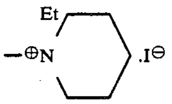 | >100 | >100 | >100 | >100 | >100 | >100 |
| 27 | H | H | H | H | 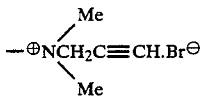 | 100 | 100 | 100 | 100 | >100 | >100 |
| 28 | H | H | $COCH_3$ | $COCH_3$ | 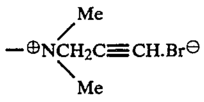 | 50 | 50 | 50 | 50 | >100 | >100 |
| 29 | H | H | $COCH_3$ | $COCH_3$ | 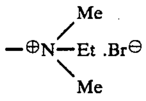 | 100 | 50 | 100 | 100 | >100 | >100 |

TABLE 1-1-continued
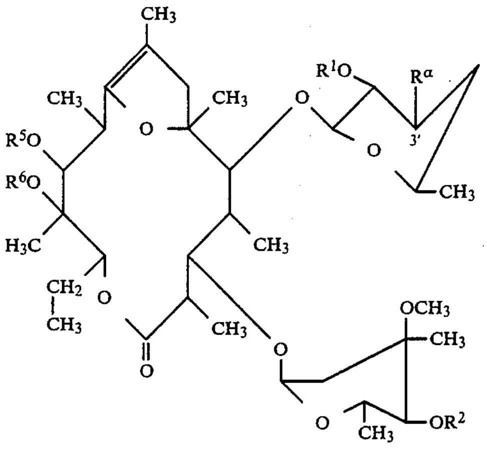
| No. | Compound (I) R[1] | R[2] | R[5] | R[6] | R[α] | MIC SA (1) | SA (2) | BS | BC | EC | KP |
|---|---|---|---|---|---|---|---|---|---|---|---|
| 30 | H | H | H | H | 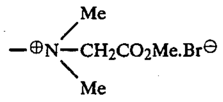 | >100 | >100 | >100 | >100 | >100 | >100 |
| 31 | H | H | H | H | 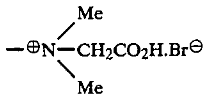 | >100 | >100 | >100 | >100 | >100 | >100 |
| 32 | H | H | H | H | 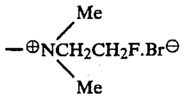 | >100 | >100 | >100 | >100 | >100 | >100 |
| 33 | H | H | H | H | 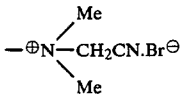 | >100 | >100 | >100 | >100 | >100 | >100 |
| 34 | H | H | H | H | 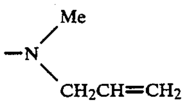 | >100 | >100 | >100 | >100 | >100 | >100 |
| 35 | H | H | H | H | 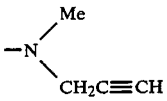 | >100 | >100 | >100 | >100 | >100 | >100 |
| 36 | H | H | H | H | 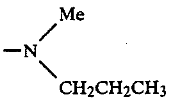 | >100 | >100 | >100 | >100 | >100 | >100 |
| 37 | H | H | H | H | 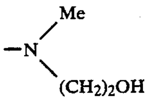 | >100 | >100 | >100 | >100 | >100 | >100 |
| 38 | H | H | H | H | 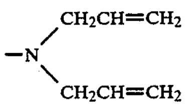 | >100 | >100 | >100 | >100 | >100 | >100 |
| 39 | H | H | H | H | $-NHCH_2CH{=}CH_2$ | >100 | >100 | >100 | >100 | >100 | >100 |

TABLE 1-1-continued
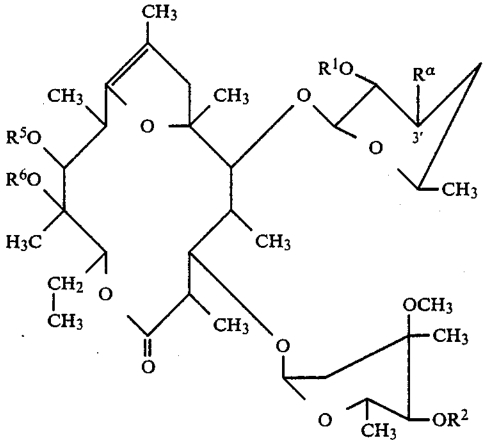
| | Compound (I) | | | | | MIC | | | | | |
|---|---|---|---|---|---|---|---|---|---|---|---|
| No. | $R^1$ | $R^2$ | $R^5$ | $R^6$ | $R^\alpha$ | SA (1) | SA (2) | BS | BC | EC | KP |
| 40 | H | H | H | H | 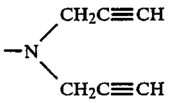 | >100 | >100 | >100 | >100 | >100 | >100 |
| 41 | H | H | H | H | $-NHCH_2C{\equiv}CH$ | >100 | >100 | >100 | >100 | >100 | >100 |
| 42 | H | H | H | H | 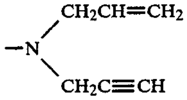 | >100 | >100 | >100 | >100 | >100 | >100 |
| 43 | H | H | H | H | 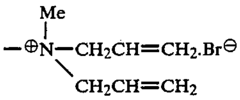 | 100 | 100 | >100 | >100 | >100 | >100 |
| 44 | H | H | H | H | 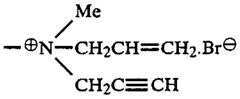 | >100 | 100 | >100 | >100 | >100 | >100 |
| 45 | H | H | H | H | 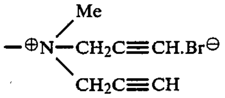 | 100 | 100 | >100 | >100 | >100 | >100 |
| 46 | H | H | H | H | 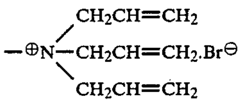 | >100 | >100 | >100 | >100 | >100 | >100 |
| 47 | H | H | H | H | 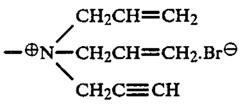 | 100 | 100 | 100 | 50 | >100 | >100 |
| 48 | H | H | H | H | 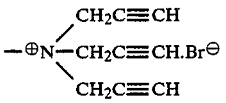 | 100 | 100 | 100 | 100 | >100 | >100 |
| 49 | H | H | H | H | 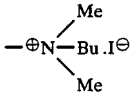 | 100 | 100 | >100 | >100 | >100 | >100 |

TABLE 1-1-continued
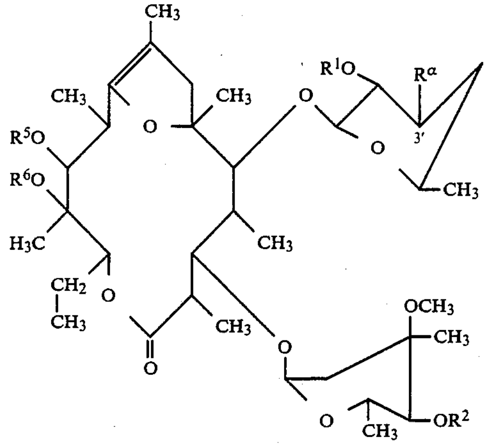
| | Compound (I) | | | | | MIC | | | | | |
|---|---|---|---|---|---|---|---|---|---|---|---|
| No. | $R^1$ | $R^2$ | $R^5$ | $R^6$ | $R^\alpha$ | SA (1) | SA (2) | BS | BC | EC | KP |
| 50 | H | H | H | H | 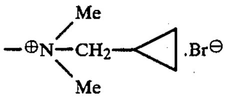 | 100 | >100 | >100 | — | >100 | >100 |
| 51 | H | H | H | H | 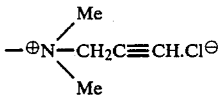 | >100 | >100 | >100 | >100 | >100 | >100 |
| 52 | H | H | $COCH_3$ | $COCH_3$ | $-NHCH_3$ | >100 | >100 | >100 | >100 | >100 | >100 |
| 53 | H | H | $COCH_3$ | $COCH_3$ | 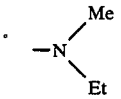 | >100 | >100 | >100 | >100 | >100 | >100 |
| 54 | H | H | 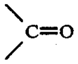 | | 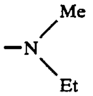 | >100 | >100 | >100 | >100 | >100 | >100 |
| 55 | H | H | 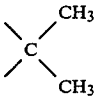 | | 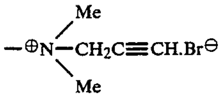 | 12.5 | 12.5 | 12.5 | 12.5 | >100 | >100 |
| 56 | H | H | 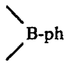 | | ( ) | 50 | 100 | 50 | 100 | >100 | >100 |
| 57 | H | H | 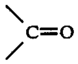 | | ( ) | 25 | 50 | 50 | 25 | >100 | >100 |
| 58 | H | CHO | H | H | 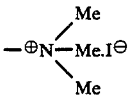 | >100 | >100 | >100 | >100 | >100 | >100 |
| 59 | H | CHO | H | H | 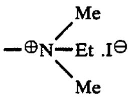 | >100 | >100 | >100 | >100 | >100 | >100 |
| 60 | H | CHO | H | H | 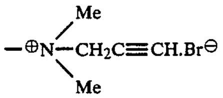 | >100 | >100 | >100 | >100 | >100 | >100 |

TABLE 1-1-continued
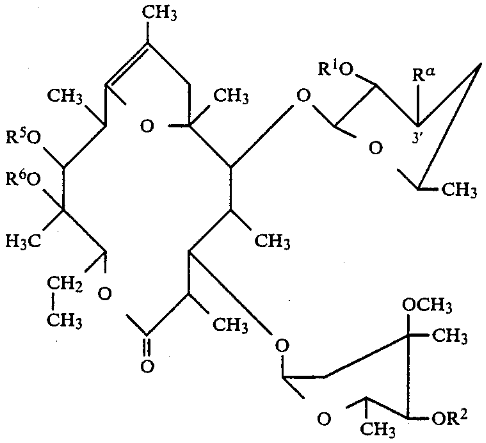
| No. | Compound (I) $R^1$ | $R^2$ | $R^5$ | $R^6$ | $R^a$ | MIC SA (1) | SA (2) | BS | BC | EC | KP |
|---|---|---|---|---|---|---|---|---|---|---|---|
| 61 | H | H | H | H | 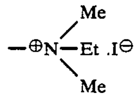 | >100 | >100 | >100 | >100 | >100 | >100 |
TABLE 2
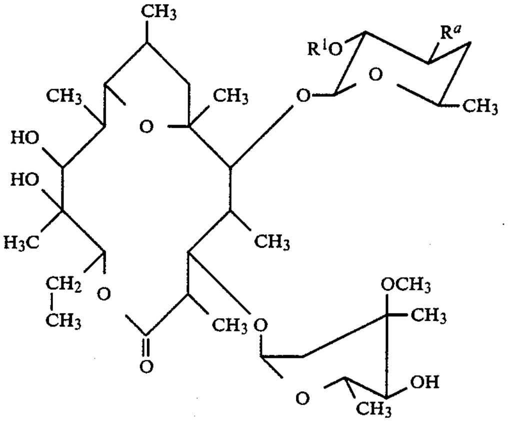
| No. | Compound (I) $R^1$ | $R^2$ | $R^a$ | MIC SA (1) | SA (2) | BS | BC | EC | KP |
|---|---|---|---|---|---|---|---|---|---|
| 62 | H | H | 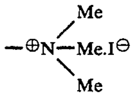 | >100 | >100 | >100 | >100 | >100 | >100 |
| 63 | H | H | 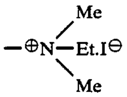 | >100 | >100 | >100 | >100 | >100 | >100 |
| 64 | H | H | 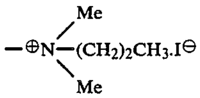 | >100 | >100 | >100 | >100 | >100 | >100 |
| 65 | H | H | 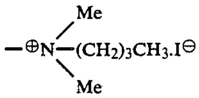 | 100 | 100 | 50 | 100 | >100 | >100 |

TABLE 2-continued
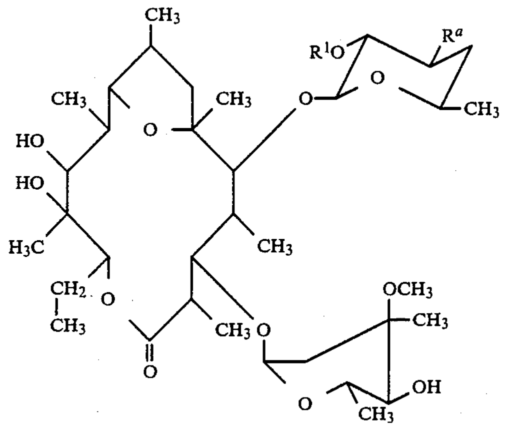
| | Compound (I) | | | MIC | | | | | |
|---|---|---|---|---|---|---|---|---|---|
| No. | $R^1$ | $R^2$ | $R^a$ | SA (1) | SA (2) | BS | BC | EC | KP |
| 66 | H | H | 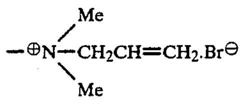 | 100 | 100 | 100 | 100 | >100 | >100 |
| 67 | H | H | 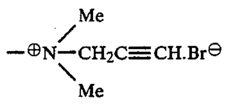 | >100 | >100 | >100 | >100 | >100 | >100 |
| 68 | $COCH_3$ | H | 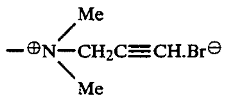 | >100 | >100 | >100 | >100 | >100 | >100 |
| 69 | H | H | 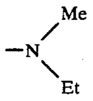 | >100 | >100 | >100 | >100 | >100 | >100 |
| *1 | H | H | $-NMe_2$ | 12.5 | 12.5 | 6.25 | 12.5 | >100 | >100 |
TABLE 3
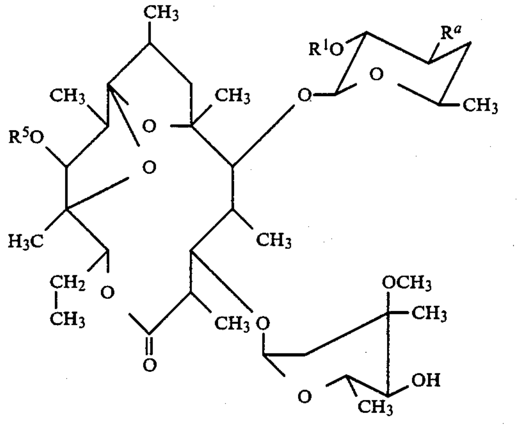
| | Compound (I) | | | MIC | | | | | |
|---|---|---|---|---|---|---|---|---|---|
| No. | $R^1$ | $R^5$ | $R^a$ | SA (1) | SA (2) | BS | BC | EC | KP |
| 70 | H | H | 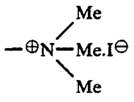 | >100 | >100 | >100 | >100 | >100 | >100 |

TABLE 3-continued
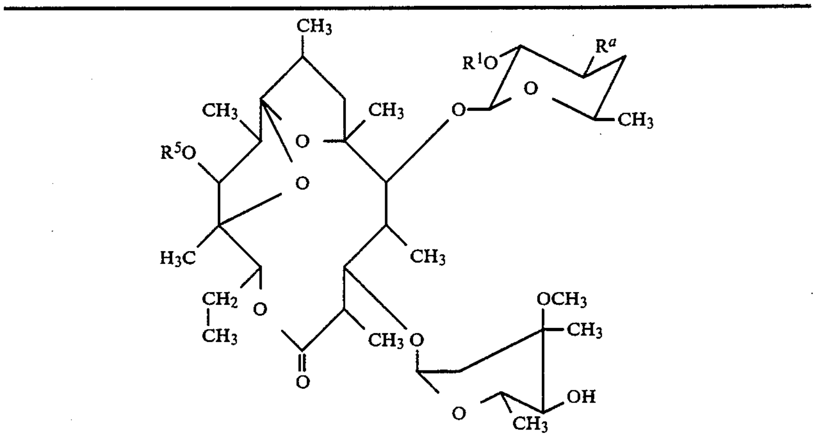
| No. | Compound (I) | | | MIC | | | | | |
|---|---|---|---|---|---|---|---|---|---|
| | $R^1$ | $R^5$ | $R^a$ | SA (1) | SA (2) | BS | BC | EC | KP |
| 71 | H | H | 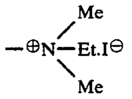 | >100 | >100 | 100 | 100 | >100 | >100 |
| 72 | H | H | 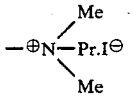 | >100 | >100 | >100 | >100 | >100 | >100 |
| 73 | H | H | 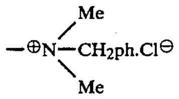 | >100 | >100 | >100 | >100 | >100 | >100 |
| *2 (EM202) | H | H | $-NMe_2$ | 12.5 | 12.5 | 6.25 | 6.25 | >100 | >100 |
*2: Anhydroerythromycin A
TABLE 4
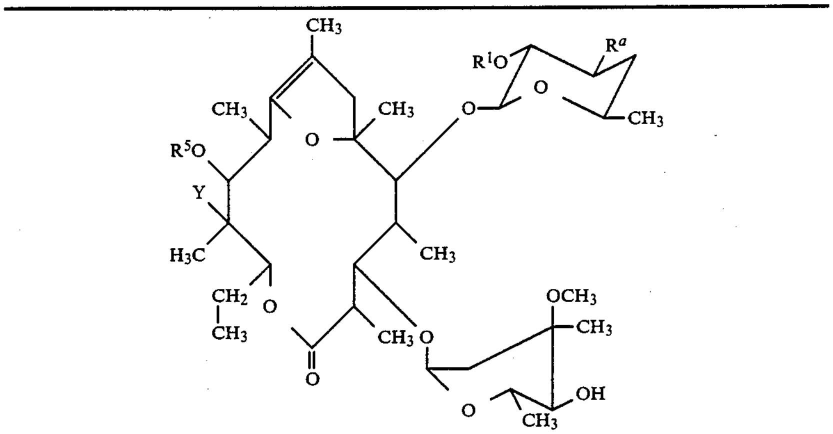
| No. | Compound (I) | | | | MIC | | | | | |
|---|---|---|---|---|---|---|---|---|---|---|
| | $R^1$ | $R^5$ | Y | $R^a$ | SA (1) | SA (2) | BS | BC | EC | KP |
| 74 | H | H | H | 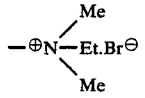 | 100 | 100 | >100 | 100 | >100 | >100 |
| 75 | H | H | H | 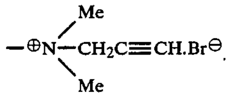 | 100 | 100 | 100 | 100 | >100 | >100 |

TABLE 5

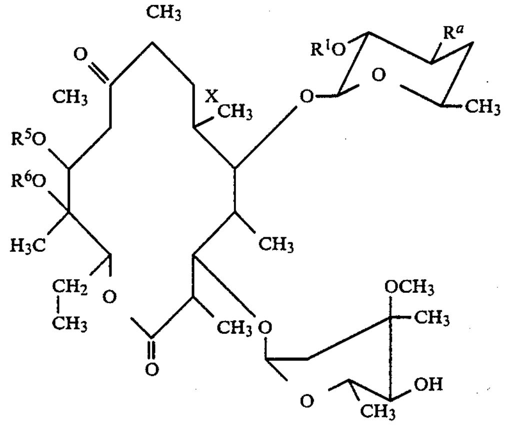

| | | | | Compound (I) | MIC | | | | | |
|---|---|---|---|---|---|---|---|---|---|---|
| No | $R^1$ | $R^5$ | $R^6$ | X | $R^a$ | SA (1) | SA (2) | BS | BC | EC | KP |
| 76 | H | H | H | OH | 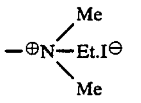 | 6.25 | 12.5 | <3.12 | 6.25 | >100 | >100 |
| 77 | H | H | H | OH | 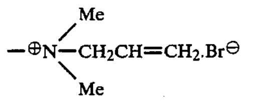 | 25 | 50 | 12.5 | 12.5 | >100 | >100 |
| 78 | H | H | H | OH | 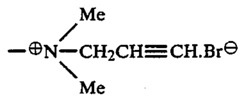 | 12.5 | 25 | 6.25 | 6.25 | >100 | >100 |
| *3 | H | H | H | OH | 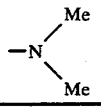 | 0.2 | 0.4 | 0.2 | 0.2 | 25 | 6.25 |

*3: Erythromycin A

Experimental Example 2

The feeds prepared by adding 0, 1.0, 10.0 and 100.0 ppm of 8,9-anhydroerythromycin A 6,9-hemiketal propargyl chloride respectively to rye-rations, were given to 160 cockerels of broilers (Habbard) of day zero, as 10 cockerels/group×4 repeats/ section, and allowed to be taken freely and continuously for 14 days. The cockerels were positioned to be accommodated for each groups by the Latin square method in an electrically heated battery brooder (the inside thereof is heated at a temperature of 32° C.). The survival rate and the growing rate were measured at 7 and 14 days of age. The result thereof is shown in Table 6.

TABLE 6

| Section No. | Administration concentration of compound (ppm) | | Survival rate (%) 0-7 days | Survival rate (%) 0-14 days | Gain (g/cockerel) 0-7 days | Gain (g/cockerel) 0-14 days |
|---|---|---|---|---|---|---|
| 1 | Control, not administrated | Mean ± | 97.5 | 97.5 | 79.5 | 245.2 |
| | | S.E. | | | 7.7 | 13.3 |
| | | (Ratio) | | | (100.0) | (100.0) |
| 2 | 1.0 | Mean ± | 97.5 | 97.5 | 84.1 | 258.2 |
| | | S.E. | | | 2.7 | 7.2 |
| | | (Ratio) | | | (105.7) | (105.3) |
| 3 | 10.0 | Mean ± | 100.0 | 100.0 | 83.5 | 254.3 |
| | | S.E. | | | 3.1 | 7.6 |
| | | (Ratio) | | | (105.0) | (103.7) |
| 4 | 100.0 | Mean ± | 100.0 | 100.0 | 88.6 | 263.3 |
| | | S.E. | | | 2.5 | 9.6 |

TABLE 6-continued

| Section No. | Administration concentration of compound (ppm) | | Survival rate (%) 0-7 days | Survival rate (%) 0-14 days | Gain (g/cockerel) 0-7 days | Gain (g/cockerel) 0-14 days |
|---|---|---|---|---|---|---|
| | | (Ratio) | | | (111.4) | (107.4) |

About 50 to 80 g of fresh excretion was collected for each groups at 0 and 7 days of age, 1 g of which was applied on a CW agar (Nissui) plate containing 5% yolk. After the anaerobic culture (BBL gas pak method) at 37° C. for 20 hours, the number of Clostridium perfringens in the excretion was counted. The result is shown in Table 7.

TABLE 7

| Section No. | Number of Cl. perfringens (log CFU/g) day 0 | Number of Cl. perfringens (log CFU/g) day 7 |
|---|---|---|
| 1 | 2.0 | 6.8 |
| 2 | 2.0 | 6.1 |
| 3 | 2.0 | 4.9 |
| 4 | 2.0 | 6.2 |

Experimental Example 3

Experimental Example 2 was repeated except for changing the administration compound to ethyl-nor-8,9-anhydroerythromycin A 6,9-hemiketal. The result of measuring the survival rate and the growing rate in cockerals of broilers (Habbard) of day zero was shown in Table 8.

TABLE 8

| Section No. | Administration concentration of compound (ppm) | | Survival rate (%) 0–7 days | Survival rate (%) 0–14 days | Gain (g/cockerel) 0–7 days | Gain (g/cockerel) 0–14 days |
|---|---|---|---|---|---|---|
| 1 | Control, not administrated | Mean ± | 97.5 | 97.5 | 83.1 | 246.6 |
| | | S.E. | | | 0.9 | 8.1 |
| | | (Ratio) | | | (100.0) | (100.0) |
| 2 | 1.0 | Mean ± | 97.5 | 97.5 | 85,7 | 263.3 |
| | | S.E. | | | 5.2 | 12.5 |
| | | (Ratio) | | | (103.1) | (106.8) |
| 3 | 10.0 | Mean ± | 97.5 | 95.0 | 81.7 | 253.1 |
| | | S.E. | | | 5.4 | 11.6 |
| | | (Ratio) | | | (98.3) | (102.6) |
| 4 | 100.0 | Mean ± | 100.0 | 100.0 | 86.7 | 259.8 |
| | | S.E. | | | 7.4 | 11.9 |
| | | (Ratio) | | | (104.3) | (105.4) |

The result of measuring the number of Clostridium perfringers in the above-described exertion was shown in Table 9.

TABLE 9

| Section No. | Number of Cl. perfringens (log CFU/g) day 0 | Number of Cl. perfringens (log CFU/g) day 7 |
|---|---|---|
| 1 | 6.65 | 7.03 |
| 2 | 7.03 | 7.20 |
| 3 | 6.83 | 7.54 |
| 4 | 6.59 | 7.17 |

Example 1

One part by weight of 8,9-anhydroerthomycin A 6,9-hemiketal propargyl chloride grounded to particles having a size of not more than 149 μm was added to 9 parts by weight of rice bran and stirred for mixing to obtain a preparation (premix) containing 10% of the erthyromycin derivative.

Example 2

The 10% preparation obtained in Example 1 was added to and mixed with the feed for the former term of broilers (see Table 10) so that the content of the preparation was adjusted to 0.2% by weight, whereby the feed for the broilers containing 200 ppm of the erythromycin derivative was obtained.

TABLE 10

(Starter for broiler feed)

| Raw material | % by weight |
|---|---|
| Corn, yellow variety | 55.55 |
| Soybean flour | 24.00 |
| White fish meal | 10.00 |
| Dried clover | 3.00 |
| Animal fats and oils | 3.00 |
| Calcium phosphate | 2.50 |
| Calcium carbonate | 1.00 |
| Salt | 0.25 |
| DL-methionine | 0.20 |
| Vitamin premix | 0.40 |
| Mineral premix | 0.10 |
| Total | 100.00 |

Example 3

The 10% preparation obtained in Example 1 was added to and mixed with the synthetic milk replacer FS-B-3 (see Table 11) so that the content of the preparation was adjusted to 0.2% by weight, whereby the feed for pigs containing 200 ppm of the erythromycin derivative.

TABLE 11

(Synthetic Milk Replacer)

| Raw material | % by weight |
|---|---|
| Corn (yellow variety) | 19.60 |
| Barley | 19.00 |
| Wheat | 15.00 |
| Soybean flour | 4.00 |
| Wheat bran | 6.80 |
| Oil cake of rice bran | 4.00 |
| White fish meal | 3.00 |
| Nonfat dry milk | 10.65 |
| Defatted soybean preparation | 5.00 |
| Whey | 5.00 |
| Sugars (grape sugar) | 5.00 |
| Animal fats and oils | 1.50 |
| Calcium phosphate (Calcium phosphate, monobasic, not less than 18% of phosphorus) | 0.70 |
| Artificial sweetener | 0.15 |
| Salt | 0.40 |
| Vitamin, mineral premix | 0.20 |
| Total | 100.00 |

Example 4

Ethyl-nor-8,9-anhydroerythromycin A 6,9-hemiketal was added to and mixed with the feed for raising calves in the nursing term, Calfmanna (registered trade mark) manufactured by Kyodo Shiryo Inc., to obtain the feed for calves containing 500 ppm of the erythromycin derivative.

The following reference, which is referred to for the disclosure at various points in this application, is incorporated herein by reference.

European Patent Publication No. EP-A-0 213 617

Antibiotics and Chemotherapy, 7, 483 (1957)

Japanese Patent Unexamined Publication No. 1588/1974

We claim:

1. A method of improving the growth of domestic animals which consists of administrating to said animals an effective growth promoting amount of a growth promoting composition containing a compound represented by the formula:

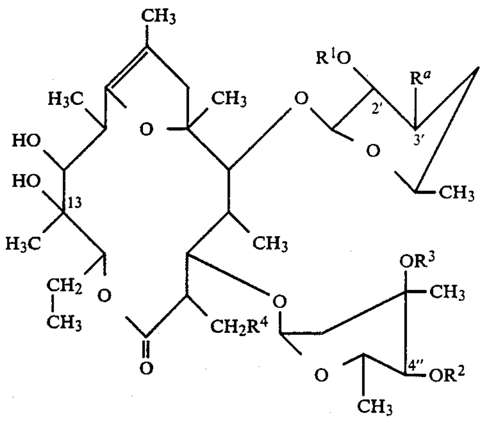

wherein;

$R^1$ is selected from the group consisting of;

a hydrogen atom; and $C_{1-5}$ alkyl carboxylic radical;

$R^2$ is a hydrogen atom;

$R^3$ is a hydrogen atom;

$R^4$ is a hydrogen atom;

$R^a$ strands for the formula

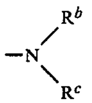

wherein $R^b$ is selected from the group consisting of:

a hydrogen atom, $C_{1-6}$ alkyl and $C_{3-7}$ cycloalkyl radical $R^c$ is selected from the group consisting of:

a hydrogen atom, $C_{1-6}$ alkyl, $C_{3-7}$ cycloalkyl, $C_{2-6}$ alkenyl and $C_{2-6}$ alkynyl radical each of which may be substituted with radicals selected from the group consisting of:

hydroxy, carboxy, $C_{1-4}$ alkoxy-carbonyl, halogen and cyano, or together $R^b$ and $R^c$ form a $C_{3-7}$ cyclic alkylamino radical together with the adjacent nitrogen atom, with the proviso that $R^c$ stands for a atom, $C_{2-6}$ alkyl, $C_{3-7}$ cycloalkyl, $C_{2-6}$ alkenyl or $C_{2-6}$ alkynyl radical when $R^b$ is a methyl radical, or $R^a$ is represented by the formula:

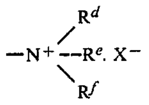

wherein each of $R^d$, $R^e$, and $R^f$, which may be the same or different, are selected from the group consisting of:

$C_{1-6}$ alkyl, $C_{3-7}$ cycloalkyl, $C_{2-6}$ alkenyl and $C_{2-6}$ alkynyl radical each of which may be substituted with radicals selected from the group consisting of:

hydroxy, carboxy, $C_{1-4}$ alkoxy-carboxyl, halogen and cyano, or together $R^d$ and $R^e$ form a $C_{3-7}$ cyclic alkylamino radical together with the adjacent nitrogen atom, and $X^-$ stands for chlorine, bromine or iodine, in an acceptable solid or liquid carrier.

2. The method of claim 1, wherein $R^d$ and $R^e$ form a cyclic alkylamino radical of 5 to 7 members, or both $R^d$ and $R^e$ are alkyl radicals having 1 to 5 carbon atoms and $R^f$ is an alkyl radical having 1 to 5 carbon atoms, an alkenyl or alkynyl radical having 2 to 6 carbon atoms.

3. The method of claim 1, wherein the erythromycin derivative is 8,9-anhydroerythromycin A 6,9-hemiketal N-propargyl chloride or N-ethyl- nor-8,9-anhydroerythromycin A 6,9-hemiketal.

4. The method of claim 1, wherein the effective growth promoting amount of the compound in the growth promoting composition is from about 0.00001 to 0.1% (w/w).

* * * * *